(12) United States Patent
Kahlman et al.

(10) Patent No.: US 8,190,372 B2
(45) Date of Patent: May 29, 2012

(54) SENSOR DEVICE FOR AND A METHOD OF SENSING MAGNETIC PARTICLES

(75) Inventors: Josephus Arnoldus Henricus Maria Kahlman, Tilburg (NL); Petrus Johannes Wilhelmus Van Lankvelt, Boekel (NL); Jeroen Hans Nieuwenhuis, Waalre (NL); Allbert Hendrik Jan Immink, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 374 days.

(21) Appl. No.: 12/528,086

(22) PCT Filed: Jun. 25, 2007

(86) PCT No.: PCT/IB2007/052449
§ 371 (c)(1),
(2), (4) Date: Aug. 21, 2009

(87) PCT Pub. No.: WO2008/102218
PCT Pub. Date: Aug. 28, 2008

(65) Prior Publication Data
US 2010/0324828 A1    Dec. 23, 2010

(30) Foreign Application Priority Data
Feb. 23, 2007  (EP) .................................. 07102984

(51) Int. Cl.
*G01N 33/543* (2006.01)

(52) U.S. Cl. .......................................................... 702/19
(58) Field of Classification Search ..................... 702/19
See application file for complete search history.

(56) References Cited

U.S. PATENT DOCUMENTS

| | | | |
|---|---|---|---|
| 2004/0207396 A1* | 10/2004 | Xiao | ............................ 324/244 |
| 2005/0035757 A1 | 2/2005 | Prins et al. | |

FOREIGN PATENT DOCUMENTS

| | | |
|---|---|---|
| EP | 1469311 A1 | 10/2004 |
| FR | 2866706 A1 | 8/2005 |
| WO | 2005010542 A1 | 2/2005 |
| WO | 2005010543 A1 | 2/2005 |
| WO | 2005111596 A1 | 11/2005 |
| WO | 2005111615 A1 | 11/2005 |

OTHER PUBLICATIONS

Michael J. Caruso, A New Perspective on Magnetic Field Sensing, © Honeywell, Inc. May 1998, p. 1-19.*

* cited by examiner

*Primary Examiner* — Tung S Lau (57) ABSTRACT

A sensor device for sensing magnetic particles, the sensor device including a substrate and a sensing unit provided on and/or in and/or near the substrate. The sensing unit is configured to sense a detection signal indicative of the presence of the magnetic particles. The sensor device further includes a magnetic field control unit which may be provided off the substrate and is configured to generate a time-dependent magnetic field for interaction with the magnetic particles.

32 Claims, 4 Drawing Sheets

SENSOR DEVICE FOR AND A METHOD OF SENSING MAGNETIC PARTICLES

FIELD OF THE INVENTION

The invention relates to a sensor device.

The invention further relates to a method of sensing magnetic particles.

Moreover, the invention relates to a program element.

Further, the invention relates to a computer-readable medium.

BACKGROUND OF THE INVENTION

A biosensor may be a device for the detection of an analyte that combines a biological component with a physicochemical or physical detector component.

Magnetic biosensors may use the Giant Magnetoresistance Effect (GMR) for detecting biological molecules being magnetic or being labeled with magnetic beads.

In the following, biosensors will be explained which may use the Giant Magnetoresistance Effect.

WO 2005/010542 discloses the detection or determination of the presence of magnetic particles using an integrated or on-chip magnetic sensor element. The device may be used for magnetic detection of binding of biological molecules on a micro-array or biochip. Particularly, WO 2005/010542 discloses a magnetic sensor device for determining the presence of at least one magnetic particle and comprises a magnetic sensor element on a substrate, a magnetic field generator for generating an AC magnetic field, a sensor circuit comprising the magnetic sensor element for sensing a magnetic property of the at least one magnetic particle which magnetic property is related to the AC magnetic field, wherein the magnetic field generator is integrated on the substrate and is arranged to operate at a frequency of 100 Hz or above.

US 2005/035757 discloses a magnetoresistive sensing device having a substrate with a layer structure for supporting a fluid. The layer structure has a first surface area in a first level and a second surface area in another second level and a magnetoresistive element for detecting the magnetic field of at least one magnetic particle in the fluid, the magnetoresistive element being positioned near a transition between the first and second surface area and facing at least one of the surface areas.

WO 2005/111596 discloses a system for distinguishing a specific binding from a less specific binding between at least one magnetic nanoparticle and a surface of another entity by applying a magnetic field and detecting a physical parameter relating to magnetic nanoparticle rotational or motional freedom while the magnetic nanoparticle is attached to the surface. The system may be applied to in-vivo and in-vitro biomolecular diagnostics. The sensor combines in one sensor the detection of magnetic particles or labels and determination of the binding quality and the properties of magnetic particles or labels which are bound to the surface of another entity.

However, sufficient accuracy of measurement results may still be problematic under undesired circumstances.

OBJECT AND SUMMARY OF THE INVENTION

It is an object of the invention to provide a sensor with a sufficiently accurate detection performance.

In order to achieve the object defined above, a sensor device for sensing magnetic particles, a method of sensing magnetic particles, a program element, and a computer-readable medium according to the independent claims are provided.

According to an exemplary embodiment of the invention, a sensor device for sensing magnetic particles is provided, the sensor device comprising a substrate and a sensing unit provided on and/or in and/or near (for instance coupled to or connected to) the substrate and being adapted for sensing a detection signal indicative of the presence of the magnetic particles, and a magnetic field control unit provided off the substrate (that is to say apart from the substrate, or outside of the substrate, particularly without contact to the substrate) and being adapted for generating a time-dependent magnetic field for interaction with the magnetic particles, particularly for guiding the magnetic particles with respect to the substrate and/or with respect to the sensing unit.

According to another exemplary embodiment of the invention, a method of sensing magnetic particles is provided, the method comprising sensing a detection signal indicative of the presence of the magnetic particles by a sensing unit provided on and/or in and/or near (for instance coupled to or connected to) a substrate, and generating a time-dependent magnetic field for interaction with the magnetic particles (particularly for guiding the magnetic particles with respect to the substrate and/or with respect to the sensing unit) by a magnetic field control unit provided off the substrate.

According to still another exemplary embodiment of the invention, a program element is provided, which, when being executed by a processor, is adapted to control or carry out a method of sensing magnetic particles having the above mentioned features.

According to yet another exemplary embodiment of the invention, a computer-readable medium is provided, in which a computer program is stored which, when being executed by a processor, is adapted to control or carry out a method of sensing magnetic particles having the above mentioned features.

The electronic sensing scheme according to embodiments of the invention can be realized by a computer program, that is by software, or by using one or more special electronic optimization circuits, that is in hardware, or in hybrid form, that is by means of software components and hardware components.

In the context of this application, the term "sample" may particularly denote any solid, liquid or gaseous substance to be analysed, or a combination thereof. For instance, the substance may be a liquid or suspension, furthermore particularly a biological substance. Such a substance may comprise proteins, polypeptides, nucleic acids, lipids, carbohydrates or full cells, etc.

The "substrate(s)" may be made of any suitable material, like glass, plastics, or a semiconductor. The term "substrate" may be thus used to define generally the elements for layers that underlie and/or overlie a layer or portions of interest. Also, the "substrate" may be any other base on which a layer is formed, for example a glass or metal layer.

The term "magnetic particles" may denote any molecules having a magnetic portion, that is to say a paramagnetic, a ferromagnetic, or a ferrimagnetic portion. Such a magnetic portion may be inherent to a specific molecule or may be attached as a separate label or bead to a molecule, for instance to a biomolecule. The term magnetic particles may refer to actual magnetic particles or to magnetizable particles (which are magnetized under the influence of an externally applied magnetic field).

The term "sensing unit" may particularly denote a portion of a sensor device at which an actual sensor event occurs or is detected, for instance a modification of a physical parameter of the sensor portion due to a hybridization between particles in the sample and capture molecules attached to a surface of the sensor portion.

The term "magnetic field control unit" may particularly denote a magnetic field actuation source for mechanically guiding or moving the magnetic particles relative to the sensing unit using magnetic forces. Such a magnetic field control unit may be provided off the substrate, that is to say may be a component which is provided separately from the substrate.

According to an exemplary embodiment of the invention, an off-chip magnetic field actuation unit may generate a time-dependent or time-varying magnetic field for guiding the magnetic particles relative to the sensing unit in a manner that an undesired interaction between different magnetic particles can be suppressed. Particularly, an oscillation-, pulsed-, step function-, or triangle function-like magnetic field includes time intervals during which such an attraction between magnetic particles is inhibited and includes time intervals during which collective actuation of magnetic particles is promoted. For instance, pauses during which no magnetic field acts on magnetic particles may be included in the time-dependent magnetic field characteristics. Thereby, it may be possible to prevent a clustering of magnetic particles for instance during accumulating the magnetic particles prior to a sensor event and/or between bound and unbound magnetic particles after a sensor event has occurred during a procedure by which unbound particles shall be washed out by magnetic forces. Therefore, the accuracy of the device may be significantly improved since undesired magnetic clustering may be avoided.

According to an exemplary embodiment of the invention, a magnetic biosensor is provided having reduced bead clustering/stacking during the preparation phase and allowing for a faster washing procedure, which may be obtained by controlling the magnetic manipulation and detection field in an intermittent manner by using pulses. Thus, pulsed magnetic actuation for biosensors may be made possible.

According to an exemplary embodiment of the invention, a biosensor is provided that measures the presence of certain biochemical agents, based on molecular capture and labelling with magnetic beads. A GMR-type magneto-resistive sensor may measure the magnetic stray-field of the bound magnetic beads. From this signal, the concentration of the biological agent may be calculated.

Magnetic actuation may be implemented in order to increase the performance of the magnetic biosensor in terms of point-of-care applications. Firstly, it allows up concentrating the magnetic particles at the sensor surface, speeding up the binding process of the magnetic particles at the sensor surface. Secondly, magnetic washing can replace the traditional wet washing step, which may be more accurate and may reduce the number of operating actions.

Compared to the chip dimensions, large external (electro-) magnets may be used for actuation in order to achieve homogeneous field gradients (forces) at the sensor surface and large penetration depths over the entire sample volume.

According to an exemplary embodiment of the invention, an advantageous manner of using the actuation magnets in terms of producing time-controlled magnetic fields is provided. These modulated magnetic fields may be used to significantly improve the performance of the biosensor in order to meet the requirements of the end-application. During magnetic attraction, pillars/chains of magnetic particles may be formed due to a local field gradient (force) around each bead that is caused by the flux guiding effect of the magnetic material inside the magnetic particles. The physical contact between the magnetic particles induces non-specific particle-particle bindings that do not break-up when the magnetic field is turned off. This forms uncontrolled clusters of magnetic particles, which are the cause of several problems:

1) It may happen that most of the magnetic particles can not reach the active sensor surface.

2) The relatively large and uncontrolled shaped clusters may give rise to a large variability of the sensor signals, which are not interpretable anymore.

During magnetic washing, pillars/chains are also formed by the same effect as during magnetic attraction. The local field gradient (force) around a bead is much larger than the one applied by the external magnet. Therefore, a single magnetic particle bound on the sensor surface can keep many un-bound magnetic particles close to the sensor surface. This effect may hamper separating the un-bound from the bound magnetic particles by magnetic washing.

According to an exemplary embodiment of the invention, pulsed magnetic actuation may be used instead of continuous actuation. Pulsed magnetic actuations means that the magnetic actuation field is switching between a high and a low magnetic field level with a certain frequency and duty cycle. During the low level part (mostly zero field) the pillar/chain of magnetic particles breaks down by the Brownian/thermal motion of the magnetic particles. This effect may give the solution of the problems described before and may also be beneficial for other actuation aspects, which are also enclosed in the embodiments.

Particularly, a pulsed magnetic field can basically be applied by two ways:

1) by an electro-magnet, which is switching between a high and a low field according to the wanted properties (for instance frequency, duty cycle etc.) and 2) a time variable field can be produced by translating and/or rotating a permanent magnet with respect to the sensor.

One embodiment is related to the reduction of cluster forming during magnetic attraction. A bond between magnetic particles can be formed while the magnetic particles are in sufficiently close proximity of each other or in physical contact with each other. It is presently believed that the interaction time plays a significant role in the chance of forming a bond. This contact time can be reduced significantly by breaking up the attraction field in short pulses. If the pulses are short enough, the thermal motion separates the particles again during the "off-time". The amplitude of the pulse during the "on-time" can be increased to reduce the loss of the time-average speed. Increasing the pulse amplitude is allowed as long as the time-average power dissipation in the electro-magnet is not significantly enlarged.

According to an exemplary embodiment of the invention, a benefit of pulsed magnetic attraction may be obtained even when cluster formation during actuation is not an issue. During attraction when the pillars/chains are formed, only the magnetic particles at the sensor surface are able to bind with the sensor surface. After the attraction field has been turned off, the other particles that were previously organized in the pillars/chains can reach the sensor surface by thermal motion and potentially form a binding. This means that there should be a time interval between magnetic attraction and magnetic washing to give all magnetic particles the opportunity to interact with the sensor surface. This time interval may increase the total measuring time, which can be disadvantageous for some applications.

Pulsed attraction may reduce the formation of pillars/chains and may enable all magnetic particles to form a binding with the sensor surface even during actuation. As a result the binding during magnetic attraction may be much faster when pulsed actuation is used (see FIG. 3 which shows measured data during actuation with and without pulsing). It can be observed that during a DC actuation the signal saturates quickly indicating a first binding of beads to the surface and a subsequent formation of pillars/chains on these beads. The initially binding beads form 'nucleation sites' for pillar formation. By applying pulsed actuation the beads continue to bind to the remaining surface because of the redistribution of beads in the "off-time" of the actuation field.

According to an exemplary embodiment of the invention, a large improvement may be obtained by pulsed magnetic actuation during a washing phase. The flux guiding effect of the magnetic particles may create an attractive force toward the particle. The attractive force of this local field gradient may typically have a range of one particle diameter; at larger distances the force of the external magnet may become dominant. For this reason two magnetic particles are attracted to each other within a distance of approximately two times their own diameter. It is believed that a particle that is bound to the sensor surface can keep an unbound particle from washing within this distance. If the density of unbound particle is high at the sensor surface, one bound magnetic particle can prevent the washing of many unbound magnetic particles. When the amount of bound particles is high, it is for an unbound particle almost impossible to escape from the sensor surface.

If it would be possible to control the above phenomenon very accurately and one bound particle would prevent a known and well-controlled amount of unbound particles from washing, then a magnetic amplification of the signal may be possible.

By using pulsed magnetic washing, the magnetic particles can escape during the "off-time" of the pulse sequence. The thermal motion of the magnetic particles may increase the distance between the particles, and when the separation becomes large enough the external magnet may be able to wash away the unbound magnetic particles. The "off-time" should be long enough to allow the average distance caused by the thermal motions to equal at least twice the particle diameter. To give an impression of this time, one may combine the needed distance with the formula of the average distance<x> that a particle travels in a time t due to Brownian motion. These times may be calculated for commonly used magnetic particle sizes, see Table 1.

TABLE 1

Appropriate "off-time" for different magnetic particle diameter in order to have effective washing actuation.

| Magnetic particle diameter [nm] | Needed "off-time" between two pulses [s] |
|---|---|
| 200 | 0.06 |
| 300 | 0.19 |
| 500 | 0.90 |
| 1000 | 7.20 |

Under DC (direct current) operation of a coil the maximum magnetic field gradient may be limited by the heat production in the actuation coils caused by the current through the wires. Using actuation without pulsing, this maximum force is not always sufficient to quickly wash away any non-specifically bound magnetic particles. This force can be increased by using pulsed actuation. Here the current may be concentrated in a pulse, which results in higher force while the time average heat production is not increased. Using pulsed magnetic actuation can increase the maximum by several orders of magnitude.

Another benefit of pulsed actuation results from higher peak currents that can be achieved during short pulses. The maximum field produced by the magnet is increased in a way that even the radial component of this field may be high enough to reset the sensor (note the sensor sensitivity may be altered due to the actuation fields that cause magnetic domains to change configuration in a magnetic layer of the sensor. resetting of these domains is then needed before readout to ensure a constant sensor sensitivity). This can avoid complex arrangements such as that of a perpendicular coil as a reset coil. This way of resetting does have several benefits such as less components and more flexibility in the cartridge design. An attraction magnet or a washing magnet can be used for resetting. Which one is better in a specific application may depend on the properties of the assay. For example, large beads may sediment in a fast manner after magnetic washing. It may happen that a magnetic measurement can only start after resetting the sensor. During the resetting, the sedimentation may cause an unwanted signal change. In that case it may be beneficial to use the washing magnet for resetting.

Kinetic measurements can be perfectly combined with pulsed actuation. If the readout time of the magnetic biosensor is short enough it can be done during the "off-time" of the pulsed actuation sequence. The sensor is reset by the previous actuation pulse. By this, kinetic measurements do not delay the total measure time of the sample.

Actuation schemes according to exemplary embodiments of the invention are not limited to the configuration with a GMR-type magneto resistive sensor. The methods can be beneficial in any assay using magnetic particle labels.

According to an exemplary embodiment of the invention, pulsed magnetic actuation of magnetic particles may be performed which may have several advantages. Firstly, it may help to prevent the formation of pillar/chains of particles during attraction, which may reduce the chance of clustering and which may speed up the binding process. The efficiency of magnetic washing can also be increased, by allow the pillars/chains to break up in between washing pulses. This may prevent unbound particles from being pulled back towards bound particles at the surface. Pulsed actuation can also be used to generate temporary larger magnetic field amplitudes to wash away non-specifically bound particles and to realize fields with actuation coils that can also be used to reset the sensor. Moreover, pulsed actuation may allow to perform kinetic measurements without slowing down the assay.

Next, further exemplary embodiments of the sensor device will be explained. However, these embodiments also apply to the method, to the program element and to the computer-readable medium.

The magnetic field control unit may be adapted for generating a pulsed magnetic field, that is a magnetic field comprising a plurality of subsequent pulses. The term "pulses" may denote an alternating sequence of different magnetic field amplitudes. Such a pulsing may suppress clustering of magnetic particles very efficiently.

The pulses may comprise a sequence of alternating first magnetic field values and second magnetic field values, wherein the absolute values of the first magnetic field values are substantially lower than the absolute values of the second magnetic field values. In particular, the first magnetic field values may be essentially zero or exactly zero, and the second magnetic field values may be significantly different from zero. In the "zero" field intervals, the magnetic particles may relax so as to suppress undesired interaction among different magnetic beads. In the "non-zero" field intervals, the magnetic particles may be collectively actuated under the influence of a magnetic field being sufficiently strong for moving the particles in a desired direction.

A duration of the first magnetic field value may be in a range between essentially 0.05 s and essentially 10 s, particularly in a range between essentially 0.2 s and essentially 1 s. The inventors have recognized that these ranges are appropriate ranges for avoiding clustering between two subsequent intervals for typical magnetic particles (see also Table 1).

In another realization of a pulsed magnetic field, the pulses of the field comprise at least two non-zero pulses with opposite sign. As each pulse of the magnetic field must either have a positive sign, a negative sign, or be zero, these two pulses can always be chosen to be consecutive non-zero pulses (with preferably one zero-pulse in between). If the pulses represent for example a component of the vector of the magnetic field strength, then pulses of "opposite sign" indicate that the corresponding components of the magnetic field point in opposite directions of space. This has the advantage that certain undesired effects (like a remaining magnetization in a magnetic particle or in the sensor unit) which are caused by the first magnetic pulse are at least partially compensated by the second, oppositely oriented magnetic pulse. Thus artifacts can be avoided and the accuracy of the measurements can be increased. It should be noted that the magnetic forces exerted on magnetic particles are not influenced by the sign of the magnetic field. In case the particles are super paramagnetic (i.e. there are no memory effects), the force is for example unaffected by an exchange of magnetic north and south poles, as it usually depends only on the field gradients.

Preferably the pulsed magnetic field comprises only such pairs of consecutive non-zero pulses in which said pulses have opposite signs. In this case, undesired effects of each "first" pulse can immediately be compensated by a following pulse. Favorably all non-zero pulses of the pulsed magnetic field belong to a sequence of pulses with alternating signs. Moreover, the non-zero pulses are preferably separated by zero-pulses (i.e. intervals with approximately zero field) to allow for the relaxation effects of the magnetic beads described above.

The time-dependent magnetic field of the sensor device is preferably generated in such a way that the temporal average of a characteristic parameter, e.g. of a spatial component of the field strength, is approximately zero. Undesired effects of the field like remaining magnetizations can thus average out over time. A zero average can for example be achieved in the case of a pulsed magnetic field if a larger number of small positive pulses is combined with a small number of correspondingly larger negative pulses. Preferably, the magnetic field comprises however at least one pair of two consecutive non-zero pulses with opposite sign that mutually compensate. A measurement after such a pair of compensating pulses will then not be disturbed by e.g. undesired remaining magnetizations. The two balanced consecutive pulses may for example have approximately equal absolute values of amplitude and duration. They may be separated by an interval of zero field or they may immediately follow one another. Preferably all pairs of consecutive non-zero pulses are balanced in such a way.

In another embodiment of the sensor device that uses a time-dependent magnetic field, this magnetic field has an envelope that gradually increases from zero to a predetermined value and/or that gradually decreases from such a predetermined value to zero. If the magnetic field comprises pulses, this is tantamount to saying that the pulse-heights gradually increase from zero or decrease to zero, respectively, wherein the definition of the "pulse-height" depends on the particular shape of the used pulses (e.g. rectangular, triangular, bell-shaped etc.). In a general definition, the pulse-height may for example be considered as the peak value that is assumed during a pulse. A sequence of pulses that gradually increase in their pulse-heights from zero to a given value may particularly be located at the start of a pulsed magnetic field. Similarly, a sequence of pulses with gradually decreasing pulse-heights is favorably used to terminate the activity of a pulsed magnetic field. The field can thus softly be blended in and/or out.

The magnetic field control unit may be adapted for generating the time-dependent magnetic field by applying a time-dependent electric excitation signal to the magnetic field control unit. By applying time-dependent voltage or current signals to coils, electromagnets or other magnetic field generating entities capable of generating a magnetic field when a current is applied, it is possible to easily generate a time-dependent magnetic field pattern and therefore magnetic field force for selectively influencing the magnetic particles. The provision of movable parts may be dispensible in such an embodiment.

Additionally or alternatively, the magnetic field control unit may be adapted for generating the time-dependent magnetic field by moving, particularly by rotating and/or by translating and/or by reciprocating (i.e. alternating the direction of motion of), the magnetic field control unit with respect to the sensing unit in a time-dependent manner. Thus, permanent magnets or electromagnets may also be moved to modulate a magnetic field acting upon the magnetic particles. An inhomogeneous spatial distribution of magnetic fields and/or a spatially dependent damping of the magnetic field may be used to modulate the influence of the generated magnetic fields so that a motion or position alteration of the magnetic field control units or magnetic field sources thereof may contribute to the modulation of the field.

The magnetic field control unit may further be adapted for attracting or repelling the magnetic particles by a correspondingly adjusted magnetic force for accumulating the magnetic particles at (a sensor active surface of) the sensing unit. Therefore, when magnetic actuation mechanisms form pillars/chains of magnetic particles, pulsed magnetic actuation may prevent undesired interaction between the particles and may allow to transport the particles to a position at which a sensor event such as a hybridization may occur.

Additionally or alternatively, the magnetic field control unit may be adapted for attracting or repelling the magnetic particles by a correspondingly adjusted magnetic force for removing unbound magnetic particles from the sensing unit. In the context of a hybridization sensor, capture molecules may be immobilized on a sensor surface and may hybridize with complementary molecules having a magnetic bead attached thereto. After such a sensor event, some of the molecules having magnetic labels remain bound to the capture molecules, whereas other molecules remain unbound in the solution. In a washing procedure, these unbound magnetic particles with corresponding molecules shall be removed from the sensor surface for a detection phase. This can be supported, according to exemplary embodiments of the invention, by a pulsed magnetic actuation thereby allowing an escape of unbound molecules from a sensor portion.

The magnetic field control unit may also be adapted as a resetting magnet, that is to say may simultaneously serve as a reset coil for resetting the sensor and as an actuation coil for moving magnetic particles. A separate coil which may be provided conventionally for such a purpose may then be dispensible.

The magnetic field control unit may comprise an electromagnet and/or a permanent magnet. Such magnets may generate inhomogeneous magnetic fields generating forces acting on the magnetic particles.

Capture molecules may be immobilized at the sensing unit. The capture molecules may be adapted for binding to complementary molecules attached to the magnetic particles by hybridization. Such a hybridization sensor may be operated advantageously with the pulsed actuation scheme according to exemplary embodiments of the invention, since a washing procedure may be significantly improved with such a technique.

The sensor device may comprise a magnetic field generator provided on and/or in the substrate and being adapted for generating a magnetic field for the detection of the presence of magnetic particles. Such a magnetic field generator may be a wire which can be actuated by an electric current so as to generate a magnetic field used for detecting the particles by a corresponding sensing portion, for instance in accordance with the GMR effect.

In a further development of the aforementioned embodiment, the sensor device comprises a control unit for supplying the magnetic field generator unit with an excitation current that has an envelope which gradually increases from zero and/or that gradually decreases to zero. Thus a slow blending in and/or out of the excitation current is achieved that allows to use higher currents which dissipate more thermal energy and thus help to erase remaining magnetizations.

The magnetic sensor device may be adapted for sensing the magnetic particles based on an effect of the group consisting of GMR, AMR, and TMR, Hall etc. Particularly, a magnetic field sensor device may make use of the Giant Magnetoresistance Effect (GMR) being a quantum mechanical effect observed in thin film structures composed of alternating (ferro)magnetic and non-magnetic metal layers. The effect manifests itself as a significant decrease in resistance from the zero-field state, when the magnetization of adjacent (ferro) magnetic layers are antiparallel due to a weak anti-ferromagnetic coupling between layers, to a lower level of resistance when the magnetization of the adjacent layers align due to an applied external field. The spin of the electrons of the non-magnetic metal align parallel or antiparallel with an applied magnetic field in equal numbers, and therefore suffer less magnetic scattering when the magnetizations of the ferromagnetic layers are parallel. Examples for biosensors making use of the Giant Magnetoresistance Effect (GMR) are disclosed in WO 2005/010542 or WO 2005/010543.

The magnetic sensor device may be adapted for sensing magnetic beads attached to biological molecules. Such biological molecules may be proteins, DNA, genes, nucleic acids, polypeptides, hormones, antibodies, etc.

Therefore, the magnetic sensor device may be adapted as a magnetic biosensor device, that is to say as a biosensor device operating on a magnetic detection principle.

At least a part of the magnetic sensor device may be realized as a monolithically integrated circuit. Therefore, components of the magnetic sensor device may be monolithically integrated in a substrate, for instance a semiconductor substrate, particularly a silicon substrate. However, other semiconductor substrates are possible, like germanium, or any group III-group V semiconductor (like gallium arsenide or the like).

The sensor can be any suitable sensor to detect the presence of magnetic particles on or near to a sensor surface, based on any property of the particles, e.g. it can detect via magnetic methods (e.g. magnetoresistive, Hall, coils), optical methods (e.g. imaging, fluorescence, chemiluminescence, absorption, scattering, surface plasmon resonance, Raman, etc.), sonic detection (e.g. surface acoustic wave, bulk acoustic wave, cantilever, quartz crystal etc.), electrical detection (e.g. conduction, impedance, amperometric, redox cycling), combinations thereof, etc.

The device and method can be used with several biochemical assay types, e.g. binding/unbinding assay, sandwich assay, competition assay, displacement assay, enzymatic assay, etc.

In addition to molecular assays, also larger moieties can be detected, e.g. cells, viruses, or fractions of cells or viruses, tissue extract, etc.

The device, methods and systems according to embodiments of the invention are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device, methods and systems described herein can be used as rapid, robust, and easy to use point-of-care biosensors for small sample volumes. The reaction chamber can be a disposable item to be used with a compact reader. Also, the device, methods and systems according to embodiments of the present invention can be used in automated high-throughput testing. In this case, the reaction chamber is e.g. a well plate or cuvette, fitting into an automated instrument.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

The illustration in the drawing is schematically. In different drawings, similar or identical elements are provided with the same reference signs.

In a first embodiment the device according to the present invention is a biosensor and will be described with respect to FIG. 1 and FIG. 2. The biosensor detects magnetic particles in a sample such as a fluid, a liquid, a gas, a visco-elastic medium, a gel or a tissue sample. The magnetic particles can have small dimensions. With nano-particles are meant particles having at least one dimension ranging between 3 nm and 5000 nm, preferably between 10 nm and 3000 nm, more preferred between 50 nm and 1000 nm. The magnetic particles can acquire a magnetic moment due to an applied magnetic field (for instance they can be paramagnetic). The magnetic particles can be a composite, for instance consist of one or more small magnetic particles inside or attached to a non-magnetic material. As long as the particles generate a non-zero response to a modulated magnetic field, that is when they generate a magnetic susceptibility or permeability, they can be used.

The device may comprise a substrate 10 and a circuit, for instance an integrated circuit.

In embodiments of the present invention, the term "substrate" may include any underlying material or materials that may be used, or upon which a device, a circuit or an epitaxial layer may be formed. In other alternative embodiments, this "substrate" may include a semiconductor substrate such as for instance a doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or an $Si_3N_4$ layer in addition to a semiconductor substrate portion. Thus, the term substrate also includes glass, plastic, ceramic, silicon-on-glass, silicon-on sapphire substrates. The term "substrate" is thus used to define generally the elements for layers that underlie a layer or portions of interest. Also, the "substrate" may be any other base on which a layer is formed, for example a glass or metal layer. In the following reference will be made to silicon processing as silicon semiconductors are commonly used, but the skilled person will appreciate that the present invention may be implemented based on other semiconductor material device(s) and that the skilled person can select suitable materials as equivalents of the dielectric and conductive materials described below.

The circuit may comprise a magneto-resistive sensor 11 as a sensor element and a magnetic field generator in the form of a conductor 12. The magneto-resistive sensor 11 may, for example, be a GMR or a TMR type sensor. The magneto-resistive sensor 11 may for example have an elongated, for instance a long and narrow stripe geometry but is not limited to this geometry. Sensor 11 and conductor 12 may be positioned adjacent to each other within a close distance g. The distance g between sensor 11 and conductor 12 may for example be between 1 nm and 1 mm; for instance 3 µm. The minimum distance is determined by the IC process.

Figure 1:
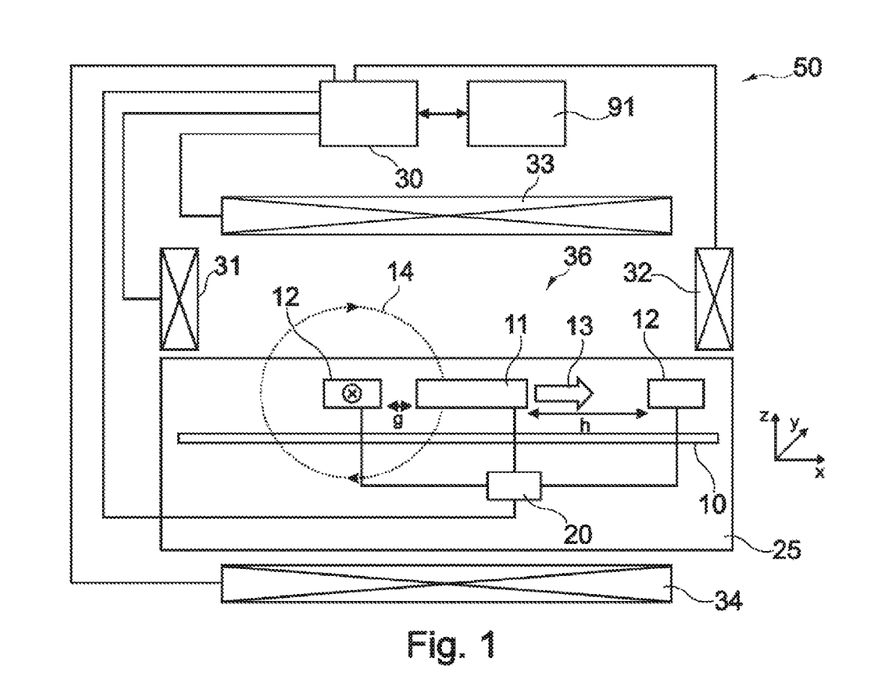
FIG. 1 illustrates a magnetic sensor device according to an exemplary embodiment in a first operation state.
Figure 2:
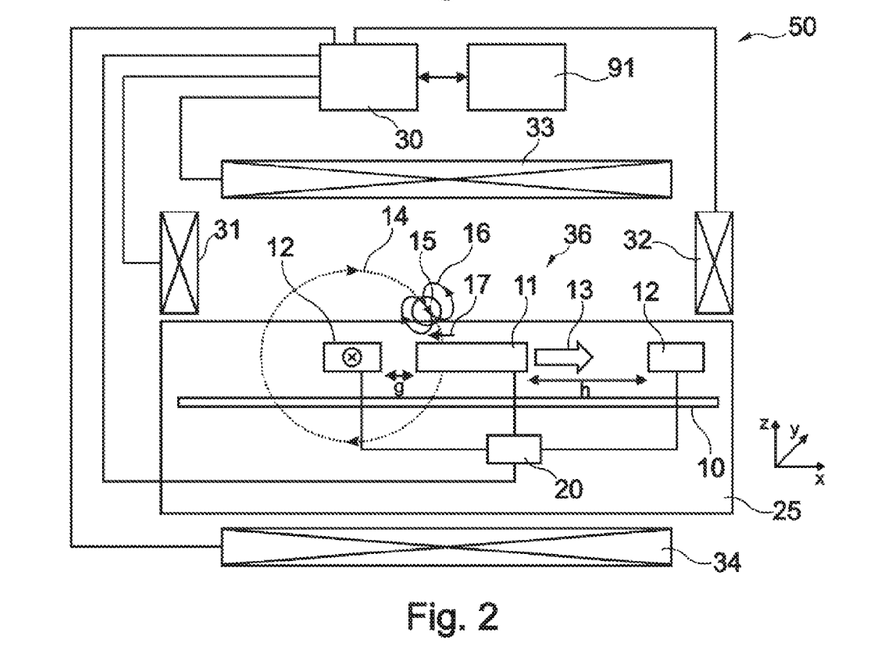
FIG. 2 illustrates the magnetic sensor device of FIG. 1 in a second operation state.

In FIG. 1 and FIG. 2, a co-ordinate device is introduced to indicate that if the sensor device is positioned in the xy plane, the sensor 11 mainly detects the x-component of a magnetic field, that is the x-direction is the sensitive direction of the sensor 11. The arrow 13 in FIG. 1 and FIG. 2 indicates the sensitive x-direction of the magneto-resistive sensor 11 according to the present invention. Because the sensor 11 is hardly sensitive in a direction perpendicular to the plane of the sensor device, in the drawing the vertical direction or z-direction, a magnetic field 14, caused by a current flowing through the conductor 12, is not detected by the sensor 11 in absence of magnetic nano-particles 15. By applying a current to the conductor 12 in the absence of magnetic nano-particles 15, the sensor 11 signal may be calibrated. This calibration is preferably performed prior to any measurement.

When a magnetic material (this can for instance be a magnetic ion, molecule, nano-particle 15, a solid material or a fluid with magnetic components) is in the neighborhood of the conductor 12, it develops a magnetic moment m indicated by the field lines 16 in FIG. 2.

The magnetic moment m then generates dipolar stray fields, which have in-plane magnetic field components 17 at the location of the sensor 11. Thus, the nano-particle 15 deflects the magnetic field 14 into the sensitive x-direction of the sensor 11 indicated by arrow 13 (FIG. 2). The x-component of the magnetic field Hx which is in the sensitive x-direction of the sensor 11, is sensed by the sensor 11 and depends on the number of magnetic nano-particles 15 and the conductor current Ic.

For further details of the general structure of such sensors, reference is made to WO 2005/010542 and WO 2005/010543.

As can be taken from FIG. 1, the sensor device 50 for sensing magnetic particles 15, comprises components integrated in a substrate 25. The sensing unit 11, 20 is partially provided in the substrate 25 and is partially provided on the substrate 25 and is adapted for sensing a detection signal indicative of the presence of the magnetic particles. Such detection signals generated by the interaction of the components 12 and 11 may be detected by the control unit 20.

Off the substrate 25, that is to say apart from the substrate 25 or outside of the substrate 25, a magnetic field control unit 30 to 34 is provided which may generate a time-dependent magnetic field for guiding the magnetic particles 15 with respect to the sensing unit 11, 20.

This magnetic field control unit 30 to 34 may include a processor 30 for controlling the procedures to be carried out. The control unit 30 may be a microprocessor or a CPU (central processing unit) and may bidirectionally communicate with an input/output device 91.

The input/output device 91 may allow a user to control operation of the device 50 and may for instance comprise a display unit like a TFT or a LCD or a plasma display. The input/output unit 91 may further comprise input elements like a keypad, a trackball, a joystick or even a microphone of a voice recognition system.

The magnetic field control unit 30 to 34 further comprises magnetic coils 31, 32, 33 and 34 which can be actuated individually or collectively by an electronic signal generated by the CPU 30.

The coils 31 and 32 are arranged to face each other along a horizontal surface of the substrate 25, whereas the coils 33 and 34 are arranged to face each other along a vertical surface of the substrate 25. Each of the coils 31 to 34 may be realized as a single coil or may comprise a plurality of coils so as to generate any desired spatial dependence of a magnetic field for mechanically guiding the molecules 15 in a sample space 36 shown in FIGS. 1 and 2. When these coils 31 to 34 have a time-dependent pulse pattern as an actuating current signal, the force acting on the magnetic particles 15 will be essentially pulse-like as well.

Figure 3:
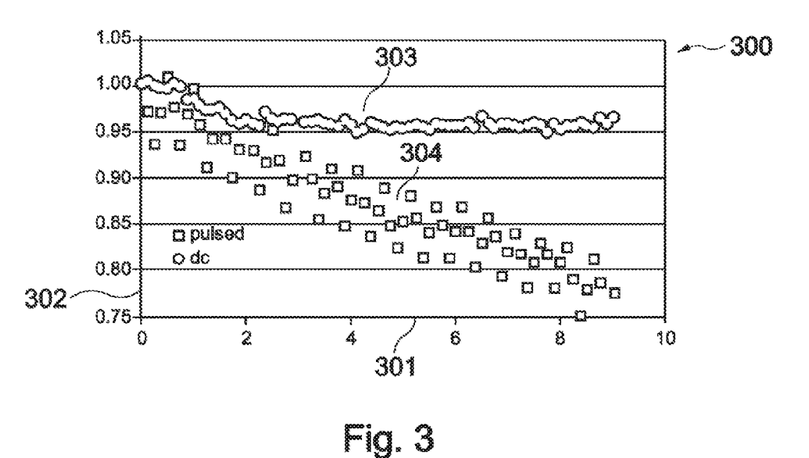
FIG. 3 shows measured sensor signals as a function of a time during actuation.

FIG. 3 shows a diagram 300 illustrating a measured sensor signal as a function of the time during actuation.

More particularly, along an abscissa 301 of the diagram 300, a time is plotted in seconds. Along an ordinate 302, a sensor signal is shown in arbitrary units. First measurement points 303 show the situation with a conventional direct current actuation signal for powering magnets of a magnetic field control unit. In contrast to this, second measurement points 304 show the situation for the pulsed application of magnetic fields for guiding the particles according to an exemplary embodiment of the invention. Thus, FIG. 3 illustrates binding by pulsed and DC attraction.

As can be taken from FIG. 3, at t=0 actuation is started. The DC signal 303 only changes in the beginning significantly, but when the pillars/chains are formed, the signal 303 does not change any more.

In contrast to this, the pulsed signal 304 according to an exemplary embodiment of the invention remains decreasing as a result of a reduced pillar/chain formation. The reason of the larger spread in the pulsed signal 304 is a consequence of the chosen read-out method for this particular measurement and is believed to have no relation to the binding process.

Figure 4:
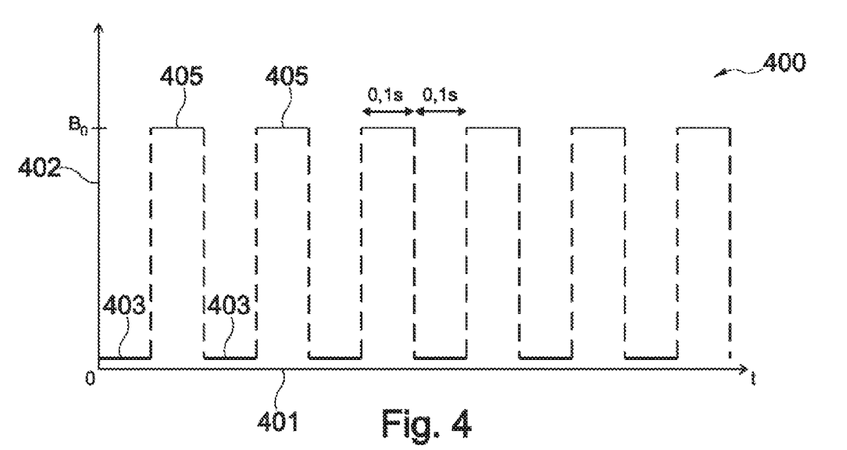
FIG. 4 illustrates a characteristic of an excitation signal applied to magnetic guiding coils (i.e. actuation coils) of a magnetic sensor device according to an exemplary embodiment.

FIG. 4 illustrates an excitation signal applied to a magnetic guiding coil of a magnetic sensor device according to an exemplary embodiment of the invention.

More particularly, FIG. 4 shows a diagram 400 having an abscissa 401 along which a time t is plotted. Along an ordinate 402 of the diagram 400, the amplitude of the generated magnetic field B is plotted. As can be taken, the time dependence of the excitation signal is a pulse function having alternating portions with a magnetic field value of essentially zero (see portions 403) and those with a significantly larger magnetic field portion (see portions 405). As can be taken from FIG. 4, the individual intervals 403, 405 may have a time duration of, for instance, 0.1 s.

During the periods 405, the magnetic particles may be moved under the influence of the gradient related to the corresponding magnetic field. During the portions 403, in which the magnetic field B is essentially zero, the particles may relax so that clustering, etc. may be efficiently avoided.

In the following, referring to FIG. 5 to FIG. 7, a sensor device 80 according to an exemplary embodiment of the invention will be explained.

Figure 5:
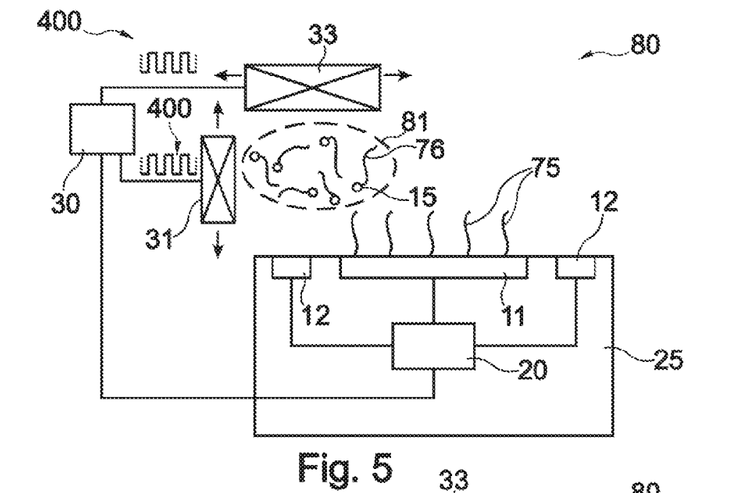
FIG. 5 to FIG. 7 illustrate a magnetic sensor device according to an exemplary embodiment of the invention in different operation states.

FIG. 5 shows the sensor device 50 in a first operation state.

Capture molecules 75 are immobilized on a sensor surface 11. A sample to be detected is located in a (virtual) volume 81 which can be defined by applying magnetic fields generating corresponding magnetic forces by the coils 31, 33. As indicated by reference numeral 400, pulses in a manner as shown in FIG. 4 are applied to both coils 33, 31 so as to avoid clustering of the molecules 15, 76 by the portions at which the magnetic field is essentially zero.

A pulse current or a constant current can be applied to the movable and vibratable coils 31, 33. By moving the coils 31, 33 and/or by modifying the applied excitation signals, the virtual volume 81 and consequently the molecules 15, 76 may be moved. By mechanically oscillating the coils 31, 33 and/or by pulsing the applied excitation signals, clustering of the molecules 15, 76 may be suppressed.

As further can be taken from FIG. 5, the beads 15 are bound to molecules 76 which can be complementary to the capture molecules 75 immobilized on the sensor surface 11. The magnetic beads 15 can actually be moved by the magnetic field gradients generated by the coils 31, 33.

FIG. 5 shows an accumulation phase in which the magnetic fields of the coils 31, 33 with the oscillating or pulsed excitation signals 400 generate forces to approach and concentrate the particles 76, 15 to be detected in an environment of the capture molecules 75.

Figure 6:
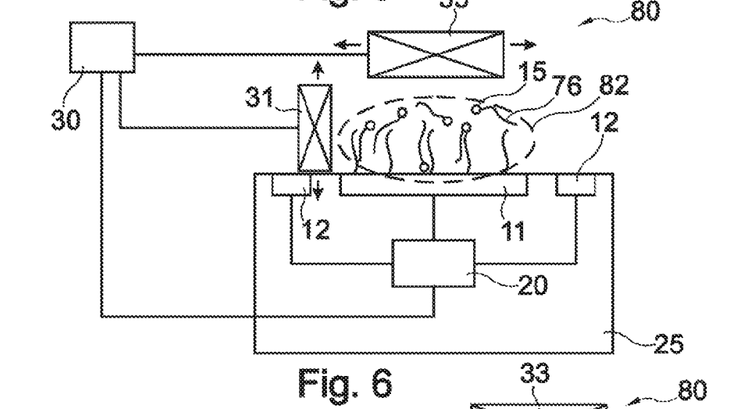

FIG. 6 shows a second operation state in which the sample volume 82 is brought to a portion close to the capture molecules 75. In the situation of FIG. 6, the coils 33, 31 with the oscillating excitation signal 400 have been moved so as to shift the sample volume from a position 81 to a position 82, and simultaneously pulses are applied for generating also a time dependence of the signals.

As can be taken from FIG. 6, some of the capture molecules 75 have immobilized with corresponding complementary molecules 76, whereas other molecules 76 with attached beads 15 do not hybridize. Before detecting the amount of particles having hybridized with the capture molecules 75, a washing procedure has to be carried out to improve accuracy.

Figure 7:
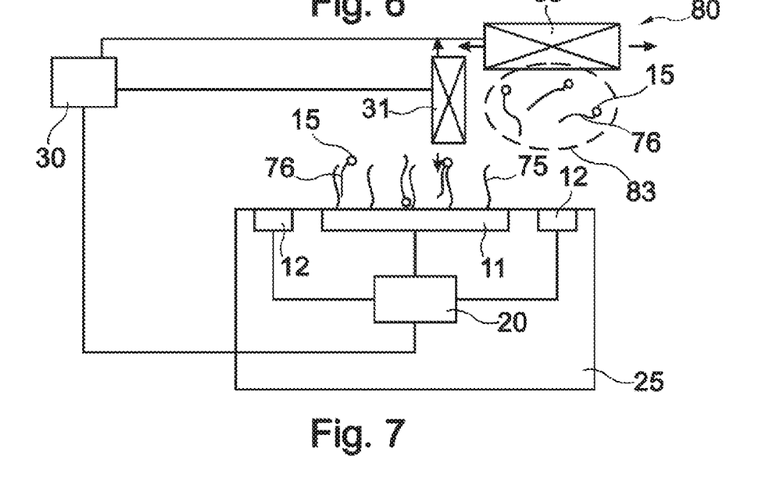

Such a magnetic washing procedure is illustrated in FIG. 7.

The sample volume has been moved to a position 83 by moving the coils 31, 33 with the oscillating excitation signals. The motion moves the sample space from a position 82 to a position 83, and the alternating pulses applied to the coils 33, 31 allow the non-bound molecules 15, 76 still provided in the volume 83 to escape from an environment of the capture molecules 75.

Therefore, as can be taken from FIG. 5 to FIG. 7, undesired clustering may be avoided during an accumulation phase (see FIG. 5) and undesired clustering may be avoided in a washing phase (see FIG. 7), due to the application of pulsed actuation signals 400 to the coils 31, 33.

Figure 8:
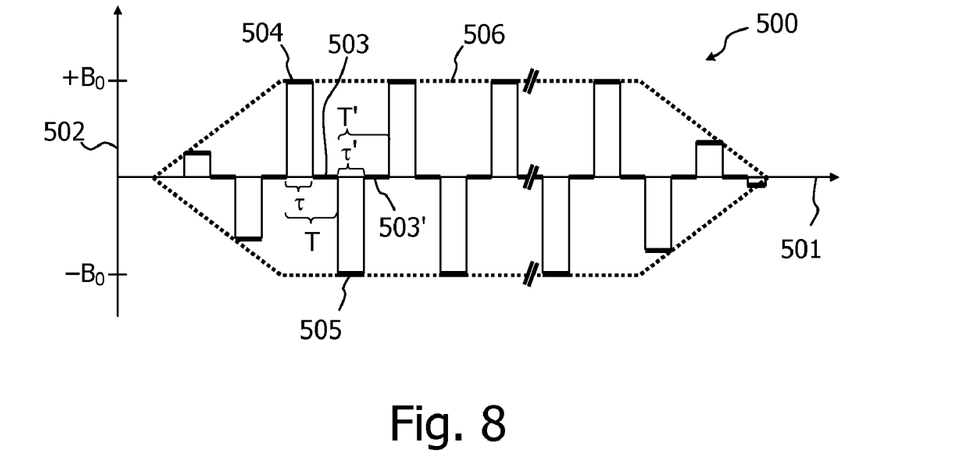
FIG. 8 illustrates an example of a magnetic actuation field in a magnetic sensor device according to an exemplary embodiment, said field comprising pulses with alternating signs.

FIG. 8 refers to a refinement of the pulse pattern of the applied magnetic field. This refinement is motivated by the observation that the sensitivity of the magnetic sensor unit and therefore the effective gain of the bio measurement are sensitive to memory effects in sensor and beads, originating from e.g. magnetic actuation fields and magnetic excitation fields in the history of the sensor. In this context, the sensitivity $s_{GMR}$ of the GMR sensor 11 shown in the previous Figures is for example defined by (with $R_{GMR}$ being the resistance and $H_{ext}$ the in-plane magnetization of the sensor):

$$s_{GMR} = \frac{dR_{GMR}}{dH_{ext}}.$$

The aforementioned effect is enhanced by the use of single polarity actuation/excitation magnetic fields, which generate a net DC magnetic field. As a result an extra reset procedure is needed for demagnetization to bring the GMR sensor in a well-defined magnetic condition after excitation. When an additional reset-coil is introduced for this purpose, this adds extra mechanical complexity. But even when the existing actuation coils 31 to 34 perform such a reset action, the disadvantage remains that they introduce a mechanical displacement on the beads and that the optimal reset amplitude is not well defined due to e.g. GMR production tolerances and in-plane actuation field tolerances (mechanical alignment of actuation-coil versus GMR). Thus the sensor will probably be set in a non-reproducible and reduced signal-to-noise ratio (SNR) operating point.

To address these problems, it is proposed to apply bipolar magnetic actuation fields, particularly with slowly increasing and/or decreasing pulse-heights. An example of such fields is shown in FIG. 8 in a diagram 500 similar to that of FIG. 4, i.e. the abscissa 501 denotes the time (in arbitrary units) and the ordinate 502 represents the amplitude of the generated pulsed magnetic field (in arbitrary units) or, equivalently, the currents that have to be applied to coils 31 to 34 for generating such a field. The pulsed magnetic field is composed of the following sub-sequence of pulses:

1) a positive pulse 504 with pulse-height ($+B_0$) and duration $\tau$;
2) a zero-field interval 503 of duration ($T-\tau$);
3) a negative pulse 505 with pulse-height ($-B_0$) and duration $\tau'$;
4) a zero-field interval 503' of duration ($T'-\tau'$).

In the shown example, the absolute amplitude values and the durations of the consecutive non-zero pulses 504, 505 are equal, i.e. $|+B_0|=|-B_0|$ and $\tau=\tau'$, and furthermore the durations of the zero-field intervals 503 and 503' are equal, i.e.

(T−τ)=(τ'−τ'). However, this is not necessarily the case. Thus a negative pulse 505 might for example immediately follow a positive pulse 504 (if T=τ) and/or have a different absolute pulse height and/or duration.

A crucial aspect of the pulse sequence 500 is that the positive and negative pulses (at least partially) compensate in the temporal average. Thus the sensor can be set to a well-defined magnetic state having a well defined DC magnetization left, which is preferably, but not limited to, zero. The zero-level of the magnetic fields or the currents used for generating them may be shifted when a net DC-magnetization is desired. It should be noted that the reversion of the field polarity will not affect the actuation mechanism as the magnetic force exerted on the magnetic beads is proportional to the square of the magnetic field strength (or of the field generating current).

FIG. 8 further shows that the absolute value of the pulse heights gradually increases from zero to the final value $|B_0|$ at the beginning of the pulse pattern 500; similarly, the pulse heights gradually decrease to zero at the and of the pulse pattern 500. Thus the envelope 506 of the pulse pattern 500 has a rhombic form, and the magnetic field activity is softly blended in and out. This has the advantage to erase any remanence magnetization in the excitation coils and the GMR sensor so that the beads are not displaced after turning off the actuation current and that the sensitivity of the GMR sensor is not changed.

An important advantage of the described "pulse compensation" is that no reset procedure and therefore no extra reset-coil are necessary. An undesired mechanical displacement of the beads during reset can thus be avoided, too. The proposed method also erases any DC magnetization present in the sensor due to magnetic fields applied in the past, e.g. during fabrication or in the logistic chain.

If the net magnetization is tuned to be zero, bead measurements are possible during the zero-field intervals 503, 503'. This enables a dynamic measuring during actuation. As also the net DC magnetization in the beads is erased in this case, the use of larger, e.g. ferro-magnetic beads becomes possible without clustering and undefined magnetic responses. Larger beads may have advantageous consequences for speeding up the assay (larger actuation forces) and for the detection SNR.

In summary, the proposed use of bipolar pulsed magnetic fields provides inter alia the following advantages:
- reduced costs as no reset coil is needed;
- better signal stability because of erasing DC magnetic fields;
- less constraints on actuation-field geometry (allowing e.g. the use of simpler coils) and mechanical alignment in terms of the in-plane magnetic field in the GMR sensor;
- higher SNR and faster assay because larger and non-super-paramagnetic beads may be used;
- dynamic measurement during actuation;
- more accurate actuation due to absence of extra reset procedure with associated bead displacement.

Figure 9:
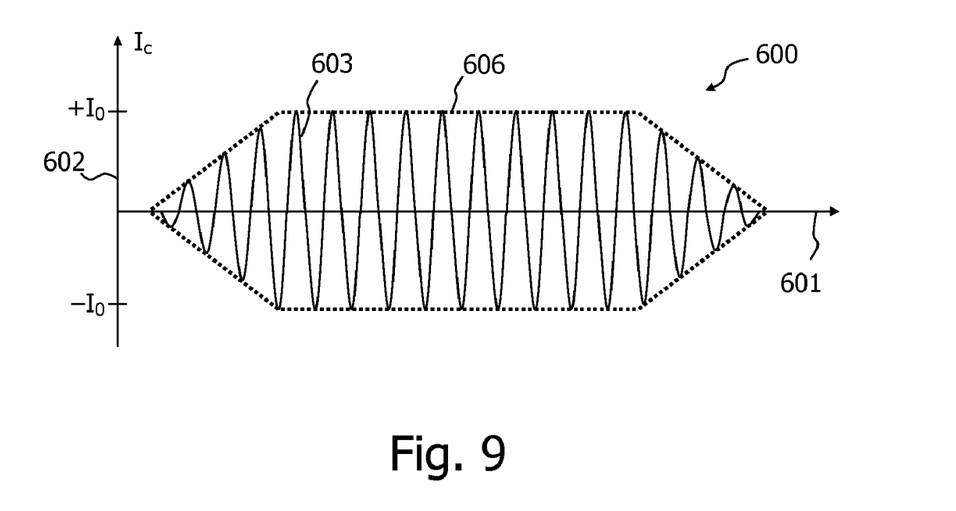
FIG. 9 illustrates the gradual switching on and off of excitation currents applied to a magnetic excitation conductor in a magnetic biosensor.

FIG. 9 shows an exemplary diagram 600 of a sinusoidal conductor current $I_c$ that is applied to the conductors 12 in the substrate for exciting the magnetic beads during their detection. The abscissa 601 of this diagram denotes the time (in arbitrary units) and the ordinate 602 the conductor current $I_c$ (in arbitrary units) or, equivalently, the in-plane magnetization due to the magnetic excitation field generated by this current. The envelope 606 of the conductor current $I_c$ has a rhombic form with a gradually increasing/decreasing amplitude at the start and at the end, respectively. This particular course of the conductor current and the associated magnetic crosstalk field can help to avoid a magnetization of the GMR sensor 11 embedded next to the conductor 12 in the substrate that would otherwise be caused by a fast switching on/off of excitation currents. Moreover, it can help to demagnetize the GMR sensor 11. Because of its slow switching on and off, the conductor current $I_c$ may be increased compared to usual detection procedures. This will generate more heat at the magneto-resistive element 11, which is beneficial to erase the DC magnetization.

It should be noted that the term "comprising" does not exclude other elements or features and the "a" or "an" does not exclude a plurality. Also elements described in association with different embodiments may be combined.

It should also be noted that reference signs in the claims shall not be construed as limiting the scope of the claims.

The invention claimed is:

1. A sensor device for sensing magnetic particles, the sensor device comprising:
   a substrate;
   a sensing unit provided near the substrate and being configured for sensing a detection signal indicative of presence of the magnetic particles and
   a magnetic field control unit provided off the substrate and being configured for generating a time-dependent magnetic field for reducing clustering of the magnetic particles in the sample volume.

2. The sensor device of claim 1,
   wherein the magnetic field control unit is configured for generating a pulsed magnetic field.

3. The sensor device of claim 1,
   wherein a temporal average of a characteristic parameter of the time-dependent magnetic field is approximately zero.

4. The sensor device of claim 1,
   wherein the time-dependent magnetic field has an envelope that gradually increases from zero and/or that gradually decreases to zero.

5. The sensor device of claim 1,
   wherein the magnetic field control unit is configured for generating the time-dependent magnetic field by applying a time-dependent electric excitation signal to at least one coil.

6. The sensor device of claim 1,
   wherein the magnetic field control unit is configured for generating the time-dependent magnetic field by moving, at least one coil with respect to the substrate in a time-dependent manner.

7. The sensor device claim 1,
   wherein the magnetic field control unit is configured for accumulating the magnetic particles in an environment of the sensing unit prior to a sensor event.

8. The sensor device of claim 1,
   wherein the magnetic field control unit is configured for removing unbound magnetic particles from the sensing unit after a sensor event.

9. The sensor device of claim 1,
   wherein the magnetic field control unit is configured for generating the time-dependent magnetic field with a frequency in a range between essentially 0.1 Hz and essentially 1 kHz.

10. The sensor device of claim 1,
    wherein the magnetic field control unit is configured as a resetting magnet.

11. The sensor device of claim 1,
    wherein the magnetic field control unit comprises at least one of the group consisting of an electromagnet and a permanent magnet.

12. The sensor device of claim 1,
further comprising capture molecules provided at a surface of the substrate and adapted-configured for binding, by hybridization, to complementary molecules attached to the magnetic particles.

13. The sensor device of claim 1,
wherein the sensor device is configured as one of the group consisting of a GMR sensor device, an AMR sensor device, a TMR sensor device, a Hall sensor device or an optical sensor using surface plasmon resonance or evanescent electromagnetic fields, or a mechanical sensor using surface acoustic waves.

14. The sensor device of claim 1,
further comprising a magnetic field generator unit provided on and/or in the substrate and being configured for generating a magnetic field for the detection of the presence of the magnetic particles.

15. The sensor device of claim 1, wherein the sample volume is guided and the clustering reduced by moving coils of the magnetic field control unit and simultaneously applying pulsed excitation signals to the moving coils for generating the time-dependent magnetic field.

16. The sensor device of claim 1, wherein an envelope of the time-dependent magnetic field has a rhombic form.

17. The sensor device of claim 1, wherein the magnetic field control unit is configured for generating the time-dependent magnetic field with a frequency between 1 Hz and 100 Hz.

18. The sensor device of claim 2,
wherein pulses of the pulsed magnetic field comprise an alternating sequence of first magnetic field values and second magnetic field values, absolute values of the first magnetic field values being substantially lower than those of the second magnetic field values.

19. The sensor device of claim 2,
wherein the pulses of the pulsed magnetic field comprise at least two non-zero pulses with opposite sign.

20. The sensor device of claim 2, wherein the pulsed magnetic field has an average value, and wherein at least one of pulse of the pulsed magnetic field has an increased amplitude and another pulse of the pulsed magnetic field has an decreased amplitude to concentrate energy in the at least one of pulse without changing the average value.

21. The sensor device of claim 2, wherein the pulsed magnetic field comprises two non-zero pulses with opposite signs and same absolute amplitudes, and wherein the two non-zero pulses are separated by an interval of zero field.

22. The sensor device of claim 14,
further comprising a control unit for supplying the magnetic field generator unit with an excitation current that has an envelope which gradually increases from zero and/or which gradually decreases to zero.

23. The sensor device of claim 18,
wherein the first magnetic field values are essentially zero and the second magnetic field values are different from zero.

24. The sensor device of claim 4,
wherein a duration of the first magnetic field value is in a range between essentially 0.05 s and essentially 10 s.

25. The sensor device of claim 18, wherein a duration of the first magnetic field value is between 0.2 s and 1 s.

26. The sensor device of claim 19,
wherein the pulses in each pair of consecutive non-zero pulses have opposite signs.

27. A method of sensing magnetic particles, the method comprising the acts of:
sensing a detection signal indicative of a presence of the magnetic particles by a sensing unit provided near a substrate;
generating a time-dependent magnetic field for interaction with the magnetic particles by a magnetic field control unit provided off the substrate; and
using the time-dependent magnetic field to reduce clustering of the magnetic particles in the sample volume.

28. A non-transitory computer readable medium embodying computer instructions which, when executed by a processor, configure the processor to perform the method of claim 27.

29. The method of claim 27, wherein the using act comprises the acts of:
moving coils of the magnetic field control unit; and
simultaneously applying pulsed excitation signals to the moving coils for generating the time-dependent magnetic field.

30. The method of claim 27, wherein the time-dependent magnetic field comprises a pulsed magnetic field having an envelope, and wherein the envelope of the time-dependent magnetic field has a rhombic form.

31. The method of claim 27, wherein the time-dependent magnetic field comprises a pulsed magnetic field, wherein the pulsed magnetic field has an average value, and wherein at least one of pulse of the pulsed magnetic field has an increased amplitude and another pulse of the pulsed magnetic field has an decreased amplitude to concentrate energy in the at least one of pulse without changing the average value.

32. The method of claim 27, wherein the time-dependent magnetic field comprises a pulsed magnetic field, and wherein the pulsed magnetic field comprises two non-zero pulses with opposite signs and same absolute amplitudes, and wherein the two non-zero pulses are separated by an interval of zero field.

* * * * *